(12) United States Patent
Ying et al.

(10) Patent No.: US 11,166,857 B2
(45) Date of Patent: Nov. 9, 2021

(54) LIQUID SENSOR FOR A DIAPER AND METHOD OF MANUFACTURING THE SAME

(71) Applicant: AGENCY FOR SCIENCE, TECHNOLOGY AND RESEARCH, Singapore (SG)

(72) Inventors: Jackie Y. Ying, Singpore (SG); Guolin Xu, Singapore (SG); Rensheng Deng, Singapore (SG); Min Hu, Singpapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/484,888

(22) PCT Filed: Feb. 8, 2018

(86) PCT No.: PCT/SG2018/050053
§ 371 (c)(1),
(2) Date: Aug. 9, 2019

(87) PCT Pub. No.: WO2018/147803
PCT Pub. Date: Aug. 16, 2018

(65) Prior Publication Data
US 2019/0374395 A1    Dec. 12, 2019

(30) Foreign Application Priority Data

Feb. 9, 2017 (SG) .......................... 10201701060P (51) Int. Cl.
*H04W 4/029* (2018.01)
*A61F 13/42* (2006.01)
(Continued)

(52) U.S. Cl.
CPC .............. *A61F 13/42* (2013.01); *G01N 27/27* (2013.01); *G01N 27/30* (2013.01); *A61F 2013/424* (2013.01)

(58) Field of Classification Search
CPC ......... A61F 13/42; A61F 13/47; G01N 27/27; G01N 27/30
(Continued)

(56) References Cited

U.S. PATENT DOCUMENTS 5,796,345 A    8/1998  Leventis et al.
5,959,535 A *  9/1999  Remsburg ............... A61F 13/42
                                                          128/886

(Continued)

FOREIGN PATENT DOCUMENTS

CN    2259883 Y    8/1997
CN    101946347 A  1/2011
(Continued)

OTHER PUBLICATIONS

Search Report and Written Opinion in International Application No. PCT/SG2018/050053 dated Apr. 17, 2018, 10 pages.

(Continued)

*Primary Examiner* — Eric Blount
(74) *Attorney, Agent, or Firm* — Marshall, Gerstein & Borun LLP (57) ABSTRACT

A liquid sensor for a diaper, and method of manufacturing the same are provided. The liquid sensor includes a plurality of electrochemical cells in series connection. Each of the plurality of electrochemical cells includes an anode, a cathode and a liquid-porous layer including an electrolyte solution. The liquid-porous layer electrically connects the anode to the cathode such that each cell has a respective predetermined potential difference across the cell. Two or more of the plurality of electrochemical cells are operable to be (Continued)

electrically connected by a liquid to form a single electrochemical cell having a potential difference lower than the sum of the predetermined potential differences of the two or more electrochemical cells.

13 Claims, 10 Drawing Sheets

(51) Int. Cl.
*G01N 27/27* (2006.01)
*G01N 27/30* (2006.01)
*H04W 4/02* (2018.01)
*H04W 4/80* (2018.01)
*G05B 11/06* (2006.01)
*G08B 21/02* (2006.01)
*H04W 4/33* (2018.01)

(58) Field of Classification Search
USPC .................................................. 340/604, 605
See application file for complete search history.

(56) References Cited

U.S. PATENT DOCUMENTS

| | | | |
|---|---|---|---|
| 6,379,835 B1 | 4/2002 | Kucherovsky et al. | |
| 10,111,787 B2 * | 10/2018 | Ying | A61F 13/49 |
| 2009/0292265 A1 * | 11/2009 | Helmer | A61F 13/42 |
| | | | 604/361 |
| 2010/0203394 A1 | 8/2010 | Bae et al. | |
| 2010/0266895 A1 | 10/2010 | Tucholski | |
| 2014/0030569 A1 | 1/2014 | Kwon et al. | |
| 2014/0147723 A1 | 5/2014 | Tucholski | |
| 2015/0209193 A1 | 7/2015 | Ying et al. | |
| 2016/0308221 A1 | 10/2016 | Siegrist | |

FOREIGN PATENT DOCUMENTS

| | | |
|---|---|---|
| CN | 102308414 A | 1/2012 |
| CN | 104884013 A | 9/2015 |
| JP | S61-167854 A | 7/1986 |
| JP | 2006-053057 A | 2/2006 |
| WO | WO-2009/085950 A2 | 7/2009 |
| WO | WO-2010/090973 A1 | 8/2010 |

OTHER PUBLICATIONS

European Search Report for application No. 18751818.8, dated Dec. 1, 2020.
Office Action in CN Application No. 201880023984.1 dated Mar. 3, 2021, 40 pages.
Office Action in CN Application No. 201880023984.1 filed Aug. 20, 2021, 13 pages.

* cited by examiner

LIQUID SENSOR FOR A DIAPER AND METHOD OF MANUFACTURING THE SAME

TECHNICAL FIELD

The present invention generally relates to a liquid sensor for a diaper, and method of manufacturing the same.

BACKGROUND ART

It is a challenge for caregivers to know when to change soiled diapers for small children and adult patients as they may not be able to effectively communicate the need for the change. The challenge for caregivers of adult patients is exacerbated by population aging, as more than one third of the population over 60 years old is expected to have problems with continence. Indeed, timely changing of soiled diapers may be especially difficult for caregivers of patients with aphasia, which is commonly caused by dementia, stroke or other advanced neurodegenerative conditions. Hence, patients may lie in soiled diapers for prolonged periods, increasing the risks of contracting diaper dermatitis, skin ulceration and infection. In addition, lying in soiled diapers over a protracted time can be incompatible with care that promotes dignity and respect for the patients.

Diaper wetness is conventionally monitored by routine manual checks, e.g. every 4 to 6 hours, where caregivers manually check the diaper of every single patient to see whether it has been soiled or not. Unfortunately, if the patient urinates/defecates shortly after the check, the patient would have to lie in a soiled diaper until the next scheduled check. On the other hand, if the diaper is dry, the diaper would not be changed and time is wasted in opening and checking unsoiled diapers. Reliance on routine manual checks is thus not the most efficient way of checking for and changing soiled diapers. Although increasing the frequency of diaper checks and change may reduce the time a patient spends in soiled diapers, the higher frequency can increase workload in manpower-constrained healthcare institutions. Alternative solutions are clearly needed.

Colorimetric-based diaper wetness indicators are conventionally used to determine the wetness of a diaper. A typical wetness indicator is positioned on the diaper exterior, and would fade and lighten when the diaper interior becomes wet. However, while colorimetric-based diaper wetness indicators can allow the diaper's wetness to be gauged without opening the diaper, the caregivers would still need to check for the color change frequently and manually. Thus, colorimetric-based diaper wetness indicators do not significantly lower labor time and costs, especially in the institutions with many patients.

Electronic humidity sensing is another approach generally used to monitor diaper wetness. Such diaper wetness sensors are based on measurement of change in conductivity using a pair of conductive electrodes. The shape of the electrodes is either in form of a wire or a pad, and the sensor is either built-in or attached to the diaper. When the diaper is wetted, the conductivity (or resistance) of the electrodes is changed. However, such sensors are usually expensive, difficult to manufacture and have a low signal-to-noise ratio.

More recently, an electrochemical sensor that adopted a different mechanism for wetness detection was disclosed. The sensor included electrodes made of two different materials which can establish a potential difference when the electrodes are bridged by the aqueous solution to be monitored. In other words, there is no potential difference or output voltage in the absence of the solution. However, the electrochemical sensor as disclosed still has a few drawbacks. For example, the sensor has a zero output voltage when the diaper is dry. If the circuit is open unintentionally for some reason (e.g. the sensor strip is broken), the output will also be zero. The inability to distinguish the two states would cause a monitoring system to incorrectly indicate that the diaper is dry even though it may not be so.

Accordingly, a need exists to provide a liquid sensor for a diaper that seeks to address some of the above problems. Furthermore, other desirable features and characteristics will become apparent from the subsequent detailed description and the appended claims, taken in conjunction with the accompanying drawings and this background of the disclosure.

SUMMARY OF INVENTION

A first aspect of the present invention provides a liquid sensor for a diaper. The liquid sensor includes a plurality of electrochemical cells in series connection. Each of the plurality of electrochemical cells includes an anode, a cathode and a liquid-porous layer including an electrolyte solution. The liquid-porous layer electrically connects the anode to the cathode such that each cell has a respective predetermined potential difference across the cell. Two or more of the plurality of electrochemical cells are operable to be electrically connected by a liquid to form a single electrochemical cell having a potential difference lower than the sum of the predetermined potential differences of the two or more electrochemical cells.

The liquid sensor may further include a removable seal encapsulating each of the plurality of electrochemical cells. The seal may be gas impermeable.

The anode of each cell may include a first end and a second end opposite the first end, the liquid-porous layer of said cell may be configured to enclose the first end, and the cathode of said cell may include a hollow cylinder configured to at least partially surround the liquid-porous layer. The hollow cylinder may include a plurality of holes formed thereon, and the second end of the anode of the cell may be configured to be enclosed by a cathode of an adjacent electrochemical cell.

The plurality of electrochemical cells may be arranged adjacent to each other to form a film, and the film may be disposed on an insulated substrate.

The liquid sensor may further include a first conductor electrically connected to one end of the plurality of electrochemical cells and a second conductor electrically connected to another end of the plurality of electrochemical cells.

The liquid sensor may further include a voltage sensor connected to the first and second conductors, the voltage sensor configured to measure a potential difference of the plurality of electrochemical cells.

The anode may include aluminum or zinc, and the cathode may include copper or graphite.

The liquid porous material may include one or more of a group consisting of: paper, cloth, polymeric absorbent and silica gel.

The plurality of electrochemical cells may be spatially distributed over a urine collection area of the diaper.

A second aspect of the present invention provides a method of manufacturing a liquid sensor. The method includes providing a plurality of electrochemical cells and connecting the plurality of electrochemical cells in series connection. Each of the plurality of electrochemical cells includes an anode, a cathode and a liquid-porous layer including an electrolyte solution, the liquid-porous layer electrically connecting the anode and the cathode such that each cell has a respective predetermined potential difference across the cell. Two or more of the plurality of electrochemical cells are electrically connectable by a liquid to form a single electrochemical cell having a potential difference lower than the sum of the predetermined potential differences of the two or more electrochemical cells The method of manufacturing the liquid sensor may further include encapsulating each of the plurality of electrochemical cells with a removable seal. The seal may be gas impermeable.

The step of providing the plurality of electrochemical cells may include providing the anode of each cell, the anode having a first end and a second end opposite the first end, enclosing the first end of said cell with the liquid-porous layer and at least partially surrounding the liquid-porous layer with the cathode of said cell, the cathode comprising a hollow cylinder having a plurality of holes formed thereon.

The step of connecting the plurality of electrochemical cells may include enclosing the second end of the anode of the cell with a cathode of an adjacent electrochemical cell.

The step of providing the plurality of electrochemical cells may include providing an insulated substrate and disposing the plurality of electrochemical cells on the insulated substrate such that the plurality of electrochemical cells are arranged adjacent to each other to form a film.

The method of manufacturing the liquid sensor may further include electrically connecting a first conductor to one end of the plurality of electrochemical cells and a second conductor to another end of the plurality of electrochemical cells.

The anode may include aluminum or zinc, and the cathode may include copper or graphite.

The liquid porous material may include one or more of a group consisting of: paper, cloth, polymeric absorbent and silica gel.

A third aspect of the present invention provides a method of detecting wetness of a diaper. The method includes disposing the liquid sensor according to the first aspect of the present invention such that the plurality of electrochemical cells are spatially distributed over a urine collection area of the diaper and detecting a reduction in an output voltage of the electrochemical cells.

BRIEF DESCRIPTION OF DRAWINGS

Embodiments of the invention will be better understood and readily apparent to one of ordinary skill in the art from the following written description, by way of example only, and in conjunction with the drawings, in which.

Skilled artisans will appreciate that elements in the figures are illustrated for simplicity and clarity and have not necessarily been depicted to scale. For example, the dimensions of some of the elements in the illustrations, block diagrams or flowcharts may be exaggerated in respect to other elements to help to improve understanding of the present embodiments.

DESCRIPTION OF EMBODIMENTS

Overview

Embodiments of the present invention seek to provide a liquid sensor that can detect presence of liquid in a diaper. The liquid sensor according to various embodiments includes a plurality of electrochemical cells in series connection. Each of the plurality of electrochemical cells includes an anode, a cathode and a liquid-porous layer comprising an electrolyte solution. In other words, the electrochemical cells are wetted to a preset level. The liquid-porous layer electrically connects the anode and the cathode such that each cell has a respective predetermined potential difference across the cell. Two or more of the plurality of electrochemical cells are operable to be electrically connected by a liquid, for example, a urine solution from a wearer of the diaper, to form a single electrochemical cell having a potential difference lower than the sum of the predetermined potential differences of the two or more electrochemical cells.

In other words, there can be a significant reduction in output voltage of the liquid sensor when two or more of the plurality of electrochemical cells are electrically connected by the liquid. Hence, the liquid sensor can provide direct output voltage with very high signal-to-noise ratio. As will be explained in detail below, the liquid sensor can possess a simple structure and can be manufactured using a cost-effective fabrication method with inexpensive materials. The liquid sensor, in various embodiments, can be embedded in proximity or within a liquid absorption layer of the diaper and can be disposable after use. Preferably, the plurality of electrochemical cells of the liquid sensor are spatially distributed over a urine collection area of the diaper. The urine collection area of the diaper can be a region on the diaper where urine of the user tends to accumulate.

Advantageously, the liquid sensor can provide a predetermined output voltage when the diaper is dry, and can provide a output voltage that is lower than the predetermined output voltage when the liquid sensor comes into contact with a liquid (e.g. body fluids such as urine), as the liquid electrically connects two or more electrochemical cells within the sensor, such that the two or more electrochemical cells form a single cell having a reduced potential difference. Particularly, as more electrochemical cells of the liquid sensor come into contact with a liquid, the potential difference across the plurality of cells can decrease further. Thus, the liquid sensor can be used to qualitatively monitor the amount of urine passed to the diaper. For example, when the liquid sensor is spatially distributed over the urine collection area of the diaper, the output voltage of the sensor can decrease with the increase of wet areas on the sensor (when more electrochemical cells are electrically connected together to form a single electrochemical cell). Further, the liquid sensor can be provided as a kit, and be attached to an inner surface of the diaper when needed. The liquid sensor can therefore be compatible with different brands and types of diapers. In alternate embodiments, the liquid sensor can also be integrated into the manufacturing process of the diapers for improved cost-effectiveness and ease of use.

Working Principle of the Liquid Sensor

The following detailed description is merely exemplary in nature and is not intended to limit the invention or the application and uses of the invention. Furthermore, there is no intention to be bound by any theory presented in the preceding background of the invention or the following detailed description. Herein, a liquid sensor for a diaper and method of manufacturing the same are presented in accordance with present embodiments having the advantages of ease of production, low cost, high signal-to-noise ratio, and compactness.

Figure 1:
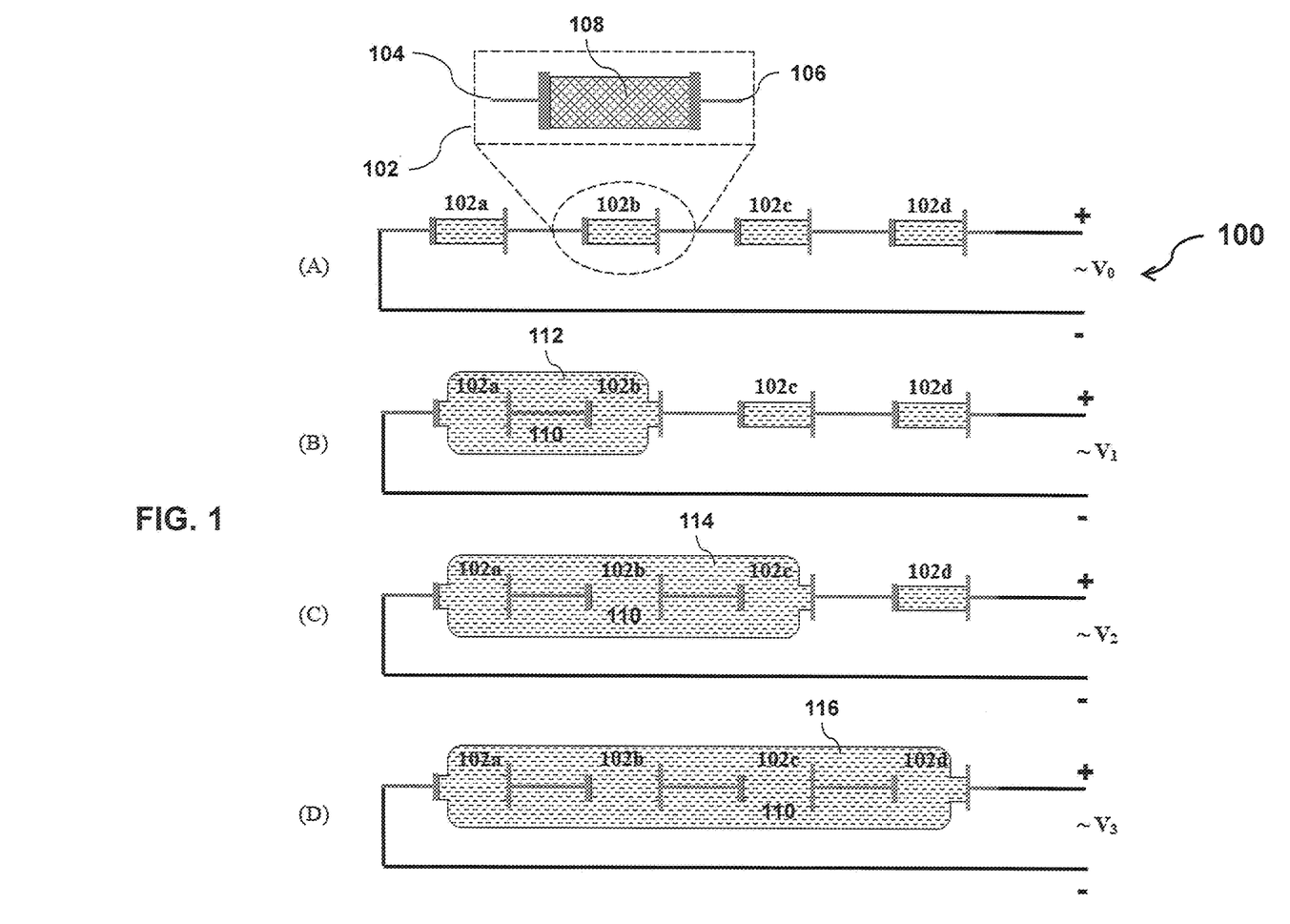
FIG. 1 shows schematic diagrams of a liquid sensor for a diaper in various states of operation, in accordance with embodiments of the invention.

FIG. 1 shows schematic diagrams of a liquid sensor 100 for a diaper in various states of operation, in accordance with embodiments of the invention. The working principle of the liquid sensor 100 and schematic design of the liquid sensor 100 are described using FIG. 1 as an exemplary embodiment. In FIG. 1, four electrochemical cells 102a, 102b, 102c, 102d are shown. However, it can be appreciated by a person skilled in the art that the number of electrochemical cells can be varied, and the configuration shown in FIG. 1 is one of the examples. Particularly, a liquid sensor can include two or more (n≥2) electrochemical cells (102a, 102b, 102c, 102d . . . 102n) joined serially to form the liquid sensor. For example, the number of electrochemical cells in the liquid sensor can be three, five or more.

An exemplary electrochemical cell 102 is shown in FIG. 1. The electrochemical cell 102 comprises an anode 104, a cathode 106 and a liquid-porous layer 108 disposed therebetween. The liquid-porous layer 108 is impregnated with an electrolyte solution, and electrically connects the anode 104 to the cathode 106. For example, the liquid-porous layer 108 is pre-wetted with a salt solution (electrolyte solution). The liquid porous layer 108 may not bounded by any waterproof layer. Thus, when an aqueous solution (e.g. urine) wets two or more electrochemical cells 102, the electrolyte solutions within the two or more electrochemical cells 102 can be electrically connected together to form a continuum. As a result, the two or more electrochemical cells 102 can form a single cell. The single cell that is formed can have a potential difference that is lower than the sum of the potential differences of the electrochemical cells 102.

With reference to FIG. 1A, each of the plurality of electrochemical cells 102a, 102b, 102c, 102d in the liquid sensor is configured to generate a predetermined potential difference across the cell. As the plurality of electrochemical cells 102a, 102b, 102c, 102d are connected in series, the liquid sensor can provide a output voltage of $V_0$ when the liquid sensor 100 is in a dry state, and the output voltage $V_0$ is equivalent to the sum of all predetermined potential differences of the electrochemical cells 102a, 102b, 102c, 102d.

FIG. 1B shows the liquid sensor 100 in a partially wetted state, with two electrochemical cells 102a, 102b connected by a liquid 110. For example, the liquid can be urine. The liquid 110 electrically connects the two electrochemical cells 102a, 102b to form a single electrochemical cell 112 having a potential difference lower than the sum of the predetermined potential differences of the two electrochemical cells 102a, 102b. The output voltage of the liquid sensor 100 is thus reduced to $V_1$, where $V_1 < V_0$. The voltage $V_1$ is the sum of the voltages of the single electrochemical cell 112 and the electrochemical cells 102c, 102d.

Further wetting of the liquid sensor 100 can occur. FIG. 10 shows the liquid sensor 100 in a further wetted state, with three electrochemical cells 102a, 102b, 102c connected by the liquid 110 to form electrochemical cell 114. The output voltage of the liquid sensor 100 is further reduced to $V_2$, where $V_2 < V_1 < V_0$. The voltage $V_2$ is the sum of the voltages of the single electrochemical cell 114 and the remaining electrochemical cell 102d.

FIG. 1D shows the liquid sensor 100 in a complete wetted stage, where the plurality of electrochemical cells 102a, 102b, 102c, 102d are connected by the liquid 110 to form electrochemical cell 116. The output voltage of the liquid sensor 100 is reduced to the lowest voltage $V_3$, where $V_3 < V_2 < V_1 < V_0$. In embodiments of the invention, the magnitude of the voltage $V_3$ can be similar or equivalent to potential difference across a single electrochemical cell formed with the anode of the electrochemical cell 102a and the cathode of electrochemical cell 102d.

As discussed above, since the output voltage of the liquid sensor 100 decreases with an increasing number of wetted electrochemical cells along the liquid sensor 100 (which can correspond to a larger wetted area on the diaper when the liquid sensor is spatially distributed over the urine collection area of the diaper), the change in output voltage of the liquid sensor 100 can be used to indicate the wetting and the wetness level of the diaper.

The principle of establishing the predetermined potential difference across the electrochemical cell 102 is now described. As aforementioned, the electrochemical cell 102 comprises the anode 104, the cathode 106 and the liquid-porous layer 108 disposed therebetween. In various embodiments of the invention, the anode 104 may include but is not limited to, aluminum or zinc, while the cathode 106 may include but is not limited to, copper or graphite. In other words, the materials suitable for preparing the anode 104 and the cathode 106 of the electrochemical cell 102 can include, but is not limited to the group consisting of zinc and copper, aluminum and copper, zinc and graphite, aluminum and graphite or any other combination known in the art that can generate a measurable potential difference in the electrochemical cell 102. Further, the electrolyte solution within the liquid-porous layer 108 can be selected from the group consisting of sodium chloride solution, potassium chloride solution, or other solutions that contain electrolytes known in the art.

In embodiments where copper/zinc electrodes are used in the electrochemical cell 102, a zinc-air cell is formed. The chemical reactions within the electrochemical cell are:
Zinc electrode (anode): $2Zn+8(OH)^- \Rightarrow 2Zn(OH)_4^{2-}+4e^-$
In the liquid: $2Zn(OH)_4^{2-} \Rightarrow 2ZnO+2H_2O+4(OH)^-$
Copper electrode (cathode): $O_2+2H_2O+4e^- \Rightarrow 4(OH)^-$
Overall reaction: $2Zn+O^2 \Rightarrow 2ZnO$ In embodiments where copper/aluminum electrodes are used in the electrochemical cell 102, an aluminum-air cell is formed. The chemical reactions within the electrochemical cell are:
Aluminum electrode (anode): $Al+3(OH)^- \Rightarrow Al(OH)_3+3e^-$
Copper electrode (cathode): $O_2+2H_2O+4e^- \Rightarrow 4(OH)^-$
Overall reaction: $4Al+3O_2+6H_2O \rightarrow 4Al(OH)_3$ As can be seen from the above reactions, oxygen present in the electrochemical cell 102 is used up. The oxygen is found mainly in the electrolyte solution, and can be used up very quickly. The oxygen thus becomes the limiting factor in the overall reaction, and can result in a significant drop in current through the electrochemical cell 102 once the overall reaction rate reduces due to the lack of oxygen. Further, as the rate of dissolution of oxygen in water is low, the current through the electrochemical cell 102 would stay low. Consequently, the anode 104 (e.g. the zinc or the aluminum electrode) would not be consumed rapidly and the electrode cell 102 could last relatively long. To further prolong the shelf life of the electrochemical cell 102, the entire liquid sensor 100 can be sealed with a removable seal to further limit continuous oxygen diffusion into the liquid-porous layer 108 of the electrochemical cell 102. In other words, each of the plurality of electrochemical cells 102 is encapsulated with a removable seal, and the seal is gas impermeable. The gas impermeable seal can be removed or broken before use to facilitate diffusion of oxygen. It can be appreciated that the entire liquid sensor 100 can be encapsulated with a gas impermeable seal, or that each electrochemical cell 102 can be individual sealed. Preservation of the liquid sensor 100 in the gas impermeable seal can also advantageously prevent the evaporation of the electrolyte solution in the liquid-porous layer 108 in addition to limiting reaction of oxygen in the air with the anode.

As can be appreciated by a person skilled in the art, the ions in the electrolyte solution (e.g. sodium and chloride ions) facilitate the reactions occurring in the electrochemical cell 102 through movement of charges between the electrodes. In embodiments of the invention, an electrolyte concentration of 0.05-3 wt % can be used to maintain functionality of the liquid sensor 100. If the salt concentration is too low (e.g. in deionized water), there may be insufficient ions for charge transfer and the electrochemical cell 102 may not function adequately, resulting in a potential difference which cannot be measured. On the other hand, high salt concentrations are unnecessary as excess salts may crystallize from solution and interfere with functionality of the liquid sensor 100 (for example, salt crystals may form on the surface of the liquid-porous layer 108 and interfere with the preservation and/or application of the liquid sensor 100 on the diaper).

The liquid-porous layer 108 disposed between the anode 104 and the cathode 106 can retain the electrolyte solution. The liquid-porous layer 108 can be a liquid absorbent material, and can include, but is not limited to paper, cloth, polymeric absorbent and/or silica gel.

Figure 2:
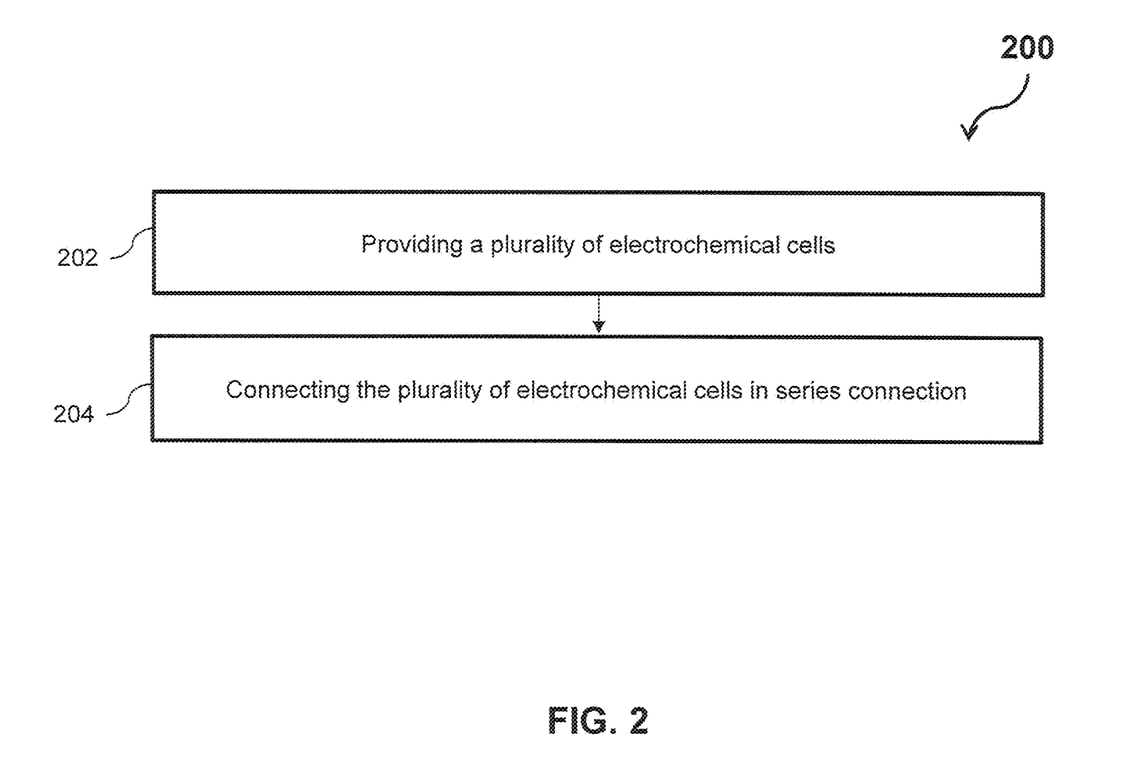
FIG. 2 shows a flowchart illustrating a method of manufacturing a liquid sensor for a diaper, in accordance with embodiments of the invention.

FIG. 2 shows a flowchart illustrating a method 200 of manufacturing a liquid sensor, in accordance with embodiments of the invention. The method 200 comprises, at step 202, providing a plurality of electrochemical cells. Each of the plurality of electrochemical cells comprises an anode, a cathode and a liquid-porous layer including an electrolyte solution. The liquid-porous layer electrically connects the anode and the cathode such that each cell has a respective predetermined potential difference across the cell. At step 204, the method 200 includes connecting the plurality of electrochemical cells in series connection. Two or more of the plurality of electrochemical cells are electrically connectable by a liquid to form a single electrochemical cell having a potential difference lower than the sum of the predetermined potential differences of the two or more electrochemical cells. Exemplary embodiments of the method 200 and the liquid sensor are described below with reference to FIGS. 3-7.

Figure 3:
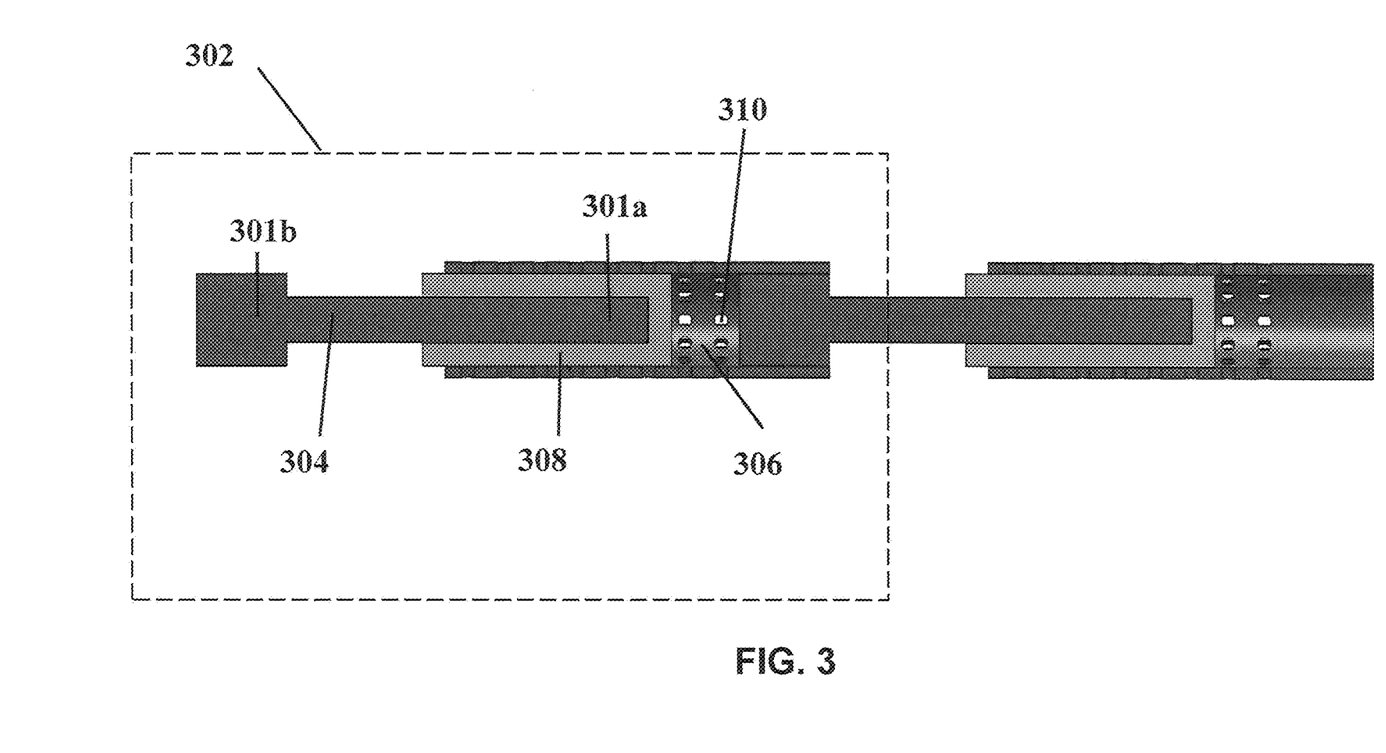
FIG. 3 shows a side cross-sectional view of an electrochemical cell used in the liquid sensor, in accordance with an embodiment of the invention.
Figure 4:
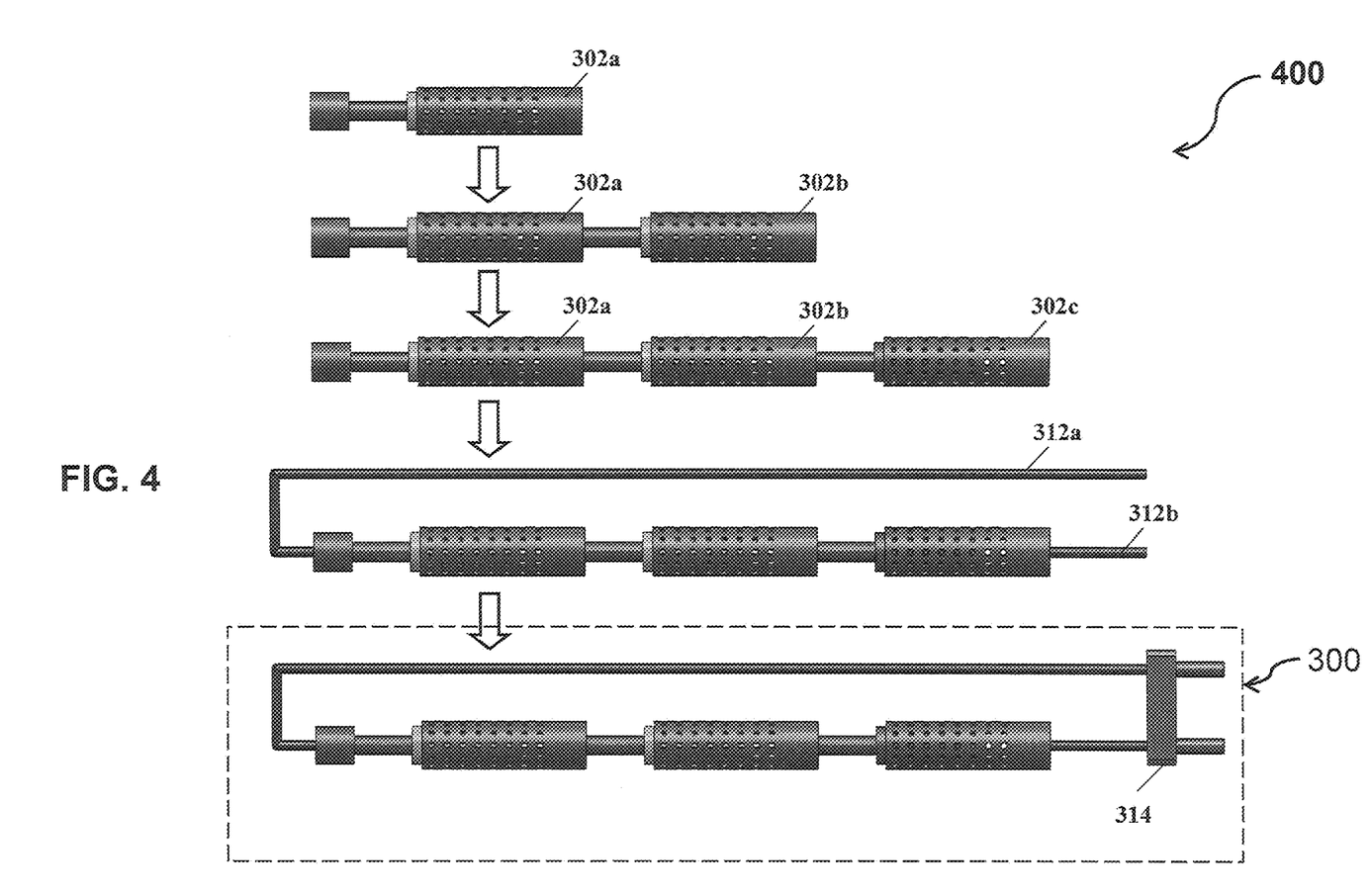
FIG. 4 shows side views of a liquid sensor using a plurality of cells as shown in FIG. 3 in various stages of assembly.

FIG. 3 shows a side cross-sectional view of an electrochemical cell 302, which can be used in the liquid sensor 300 (as shown in FIG. 4). FIG. 4 shows side views of the liquid sensor 300 using a plurality of cells 302 as shown in FIG. 3, in various stages of assembly. FIG. 3 shows the electrochemical cell 302. The electrochemical cell 302 comprises an anode 304, a cathode 306 and a liquid-porous layer 308. The electrochemical cell 302 comprises a cylindrical structure. However, it can be appreciated that the electrochemical cell 302 can have a different cross-sectional profile (e.g. polygonal) as well. As shown in FIG. 2A, the anode 304 of the electrochemical cell 302 comprises a first end 301a and a second end 301b opposite the first end 301a. The liquid-porous layer 308 of the cell 302 is configured to enclose the first end 301a, and the cathode 306 comprises a hollow cylinder configured to at least partially surround the liquid-porous layer 308. The hollow cylinder comprises a plurality of holes 310 formed thereon.

A method of assembling the electrochemical cell 302, in accordance with embodiments of the invention is briefly described. The method comprises providing the anode 304, the anode having a first end 301a and a second end 301b opposite the first end 301a. The method also comprises enclosing the first end 301a with the liquid-porous layer 308. In some embodiments, the step of enclosing the first end 301a can include inserting the first end 301a of the anode 304 into lumen of liquid porous layer 308. The method further includes connecting the liquid-porous layer 308 with the cathode 306, such that the cathode 306 at least partially surrounds the liquid-porous layer 308. The step of connecting the liquid-porous layer 308 with the cathode 306 can include pushing the anode 304 and the liquid porous layer 308 into the cathode 308. Furthermore, a plurality of electrochemical cells 302 can be assembled in series connection to form the liquid sensor 300 as shown in FIG. 4. Assembly of the plurality of electrochemical cells 302 to form the liquid sensor 300 can include connecting an anode of an adjacent electrochemical cell (not labelled) with an end of the cathode 306. For example, the second end of the anode of a cell can be enclosed by a cathode of an adjacent cell.

FIG. 4 shows that the liquid sensor 300 can be assembled by connecting each of three electrochemical cells 302a, 302b, 302c in series. The sequence 400 of assembling the liquid sensor 300 can include providing a first electrochemical cell 302a, and connecting a second electrochemical cell 302b to the first electrochemical cell 302b. The step of connecting the second electrochemical cell 302b can include inserting an end of the anode of the second chemical cell 302b into the cathode of the first electrochemical cell 302a, as shown in FIG. 4, such that the cathode of the first electrochemical cell 302b encloses the anode of the first electrochemical cell 302a. The above-mentioned steps are repeated for serially connecting a third electrochemical cell 302c to the second electrochemical cell 302b. The assembly of the liquid sensor 300 can also include connecting a first conductor 312a to one end of the plurality of electrochemical cells and a second conductor 312b to another end of the plurality of electrochemical cells. The first and second conductors 312a, 312b can be insulated wires and can link the plurality of electrochemical cells 302a, 302b, 302c to connector 314 to form an assembled liquid sensor 300. The assembled liquid sensor 300 can then be disposed onto a diaper. When a diaper wear urinates onto the liquid sensor 300, the urine can pass through the plurality of holes present on the cathode of the electrochemical cells 302a, 302b, 302c and bridge the electrolyte solutions present on the electrochemical cells 302a, 302b, 302c. The electrochemical cells 302a, 302b, 302c that are connected by the liquid would form a single electrochemical cell having a potential difference lower than the sum of the potential differences of the connected electrochemical cells 302a, 302b, 302c. The change in the output voltage (i.e. potential difference) of the liquid sensor 300 can indicate the wetting of the diaper, and the signal can be transmitted to a transmitter or a display unit via the connector 315.

Figure 5:
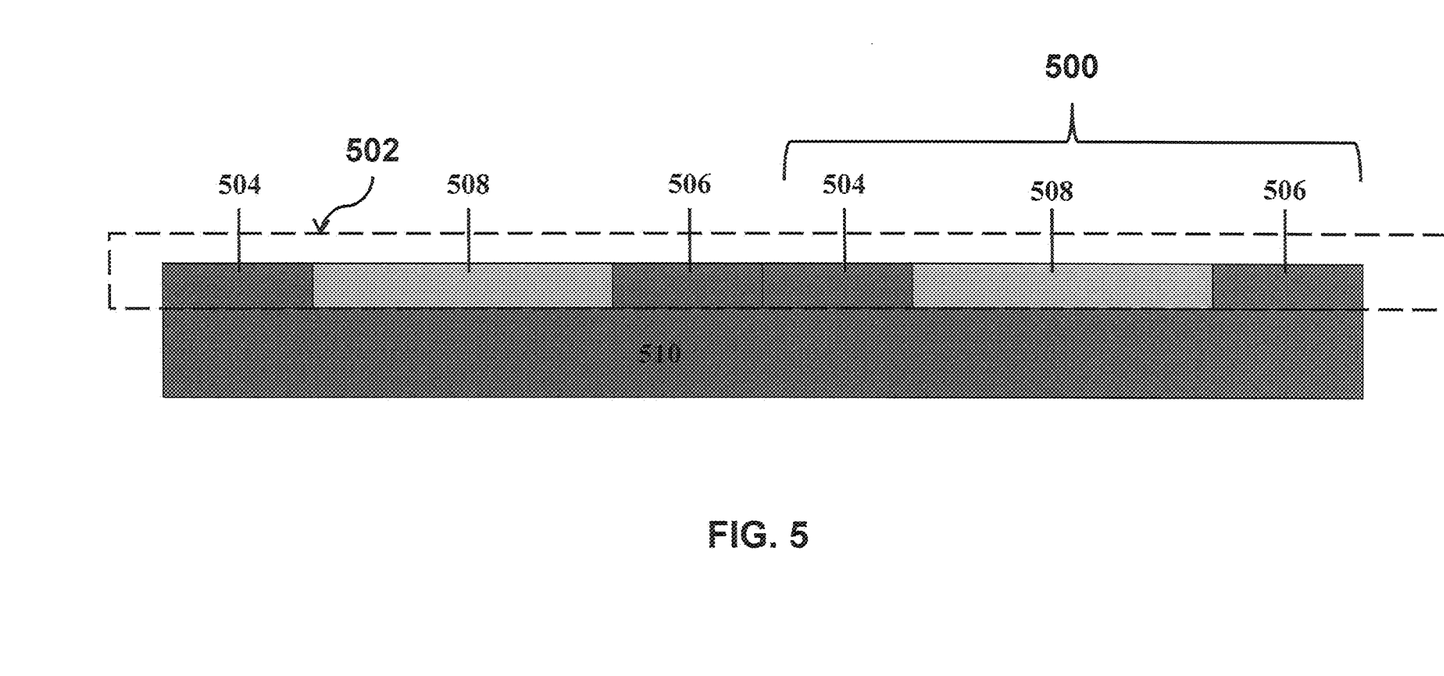
FIG. 5 shows a side cross-sectional view of electrochemical cells used in the liquid sensor, in accordance with another embodiment of the invention.
Figure 7:
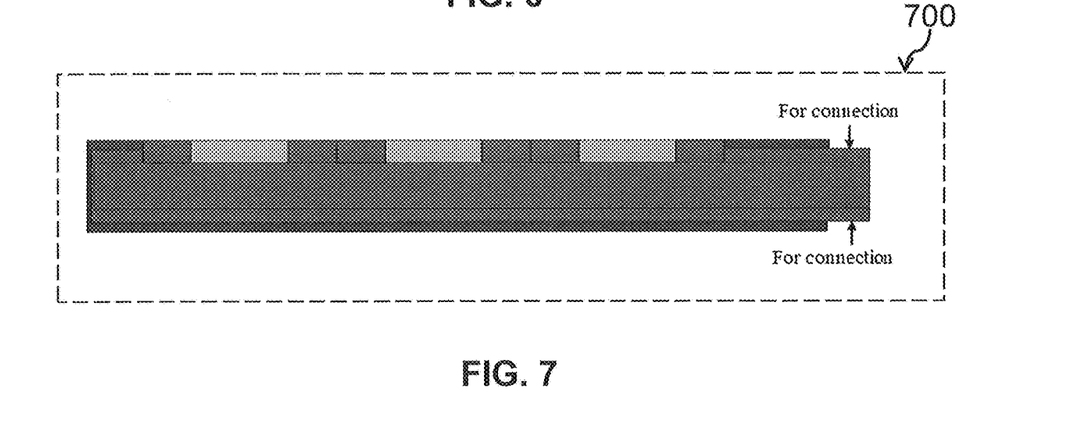
FIG. 7 shows a side cross-sectional view of a liquid sensor, in accordance with embodiments of the invention.

FIG. 5 shows a side cross-sectional view of an electrochemical cell 500 used in liquid sensor 700 (as shown in FIG. 7), in accordance with embodiments of the invention. In the liquid sensor 700, a plurality of electrochemical cells 500 are arranged adjacent to each other to form a film 502, and the film 502 is disposed on an insulated substrate 510. Each of the plurality of electrochemical cells 500 comprises an anode 504, a cathode 506 and a liquid-porous layer film 508 disposed on substrate 510. Arrangement of the plurality of electrochemical cells 500 ensures that each electrochemical cell 500 is closely connected to each other and the individual electrochemical cell 500 can be serially joined together to construct the liquid sensor 700 in the form of a sensor strip. The insulated substrate 510 in various embodiments comprises a thin sheet of electrically insulating material. The insulating material can include, but is not limited to soft polymer films or paper with waterproof coating.

Figure 6:
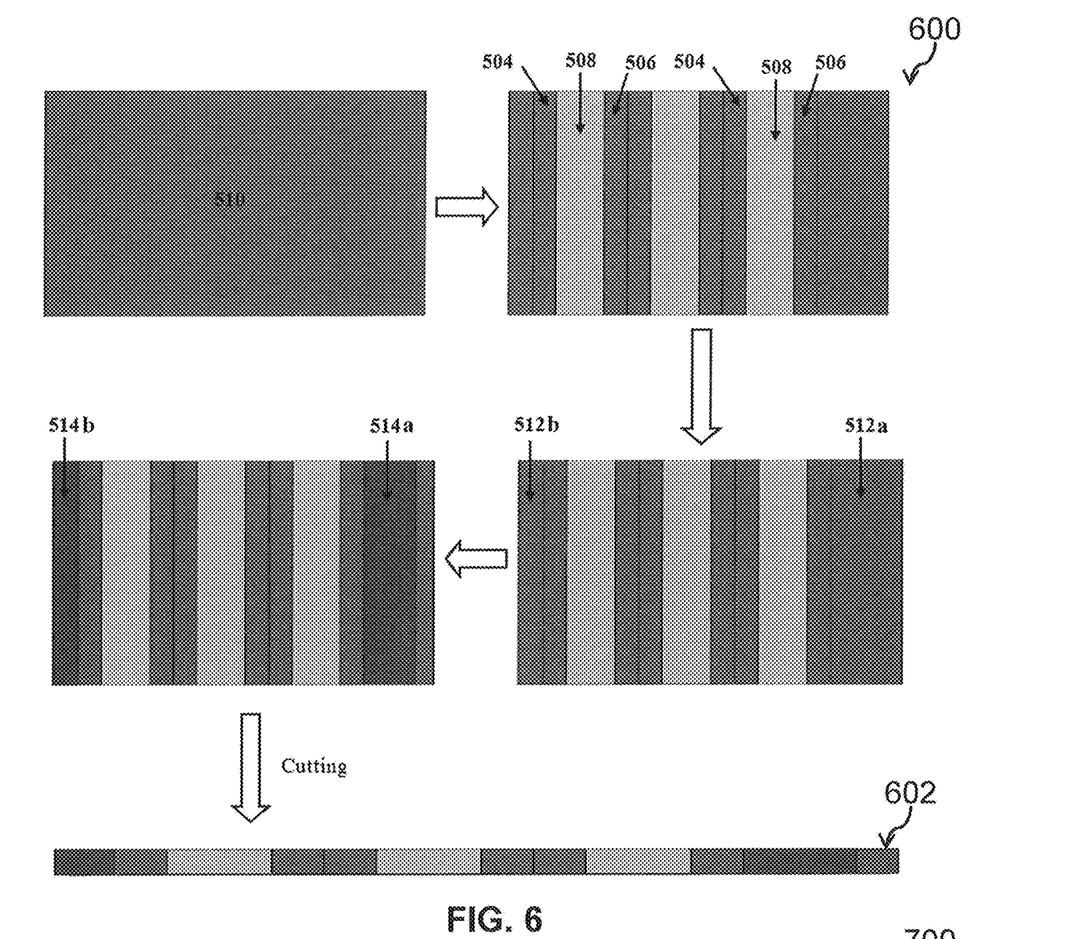
FIG. 6 shows plan views of a liquid sensor using a plurality of cells as shown in FIG. 5 in various stages of manufacture.

FIG. 6 shows plan views of a liquid sensor using a plurality of cells as shown in FIG. 5 in various stages of manufacture. In embodiments of the invention, manufacturing of the liquid sensor 700 can include laminating long film strips of the anode 504, the cathode 506 and the liquid-porous layer film 508 on substrate 510 and cutting the laminated sheet into strips 602. Laminating film strips of the anode 504, the cathode 506 and the liquid-porous layer film 508 on substrate 510 can first include disposing aligning the film strips 504, 506, 508 on the substrate 510, adhering the film strips 504, 506, 508 with adhesives either originally on the film strips (e.g. single-sided tape) or freshly applied to the substrate 510. The step of lamination can further include electrically connecting a first conductor (conductive tape 512a) to one end of the plurality of electrochemical cells and a second conductor (conductive tape 512b) to another end of the plurality of electrochemical cells. The conductive tapes 512a, 512b can connect to a voltage sensor and can facilitate measurement of the potential difference of the plurality of electrochemical cells 502. To prevent unnecessary contact with the liquid (e.g. urine), insulating tapes 514a, 514b can be disposed on the conductive tapes 512a, 512b and the insulating tapes 514a, 514b can be configured to leave only an end of the conductive tapes 512a, 512b exposed for further connection to the voltage sensor. The resulting laminated sheet is cut along a cross-sectional direction to form narrow strips 602. FIG. 7 shows a side cross-sectional view of the finished product, i.e. the liquid sensor 700. The liquid sensor 700 can further include a removable seal disposed thereon (not shown). The removable seal is gas impermeable and encapsulates each of the plurality of cells such that reaction between the anode and oxygen is limited. In embodiments of the invention, the liquid sensor 700 can be attached to the diaper and the seal is removed or broken before usage. When urine wets the liquid sensor 700 and links the pre-wetted porous layers 508 together, the output voltage from the sensor 700 would decrease as according to the wetness level of the diaper.

Performance Characterization

Figure 8A:
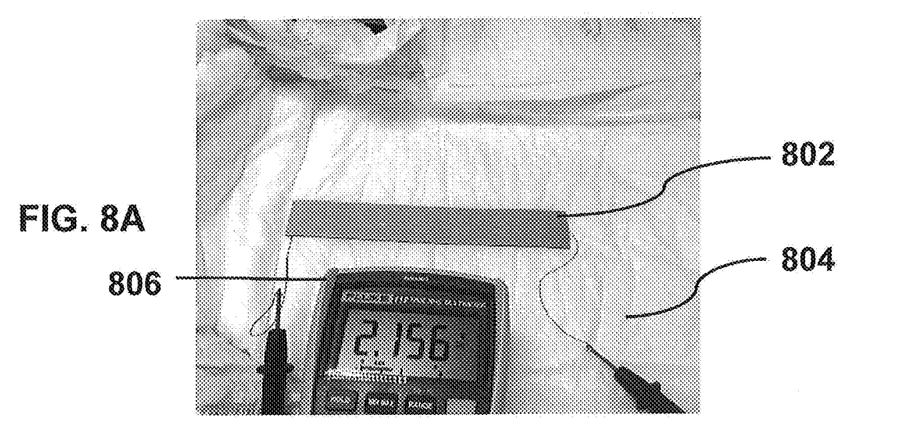
FIGS. 8a, 8b and 8c show morphology and voltage readings of a 4-electrochemical cell liquid sensor in various states of operation, in accordance with embodiments of the invention.

To characterize the performance of the liquid sensor in wetness detection, a prototype liquid sensor is used. An example of the prototype liquid sensor 802 is shown in FIG. 8. The as-fabricated prototype liquid sensor 802 has a cylindrical structure similar to that of the liquid sensor 300 shown in FIG. 4, and comprises 4 electrochemical cells. The liquid sensor 802 is attached to the inner side of diaper using a paper-based tape. To characterize the performance of a liquid sensor 802 in wetness detection, example 0.5-3 wt % sodium chloride solutions (electrolyte solutions) were introduced in 25 mL or 50 mL aliquots at a time interval of 5 min. The output voltage of the sensor was monitored continuously using a multimeter.

Figure 8B:
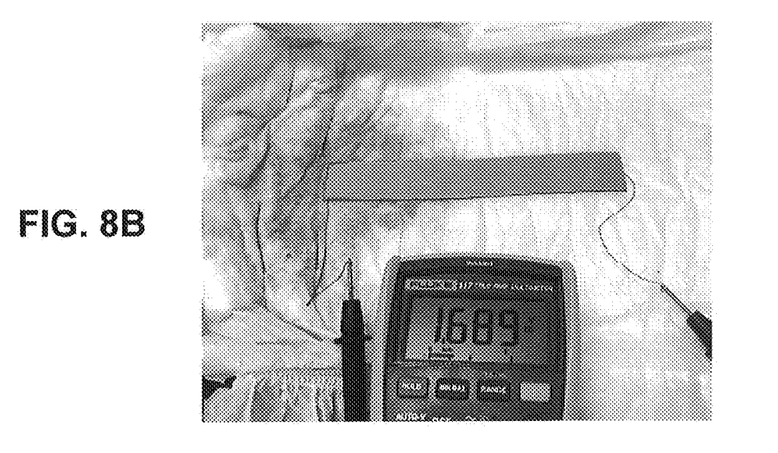
Figure 8C:
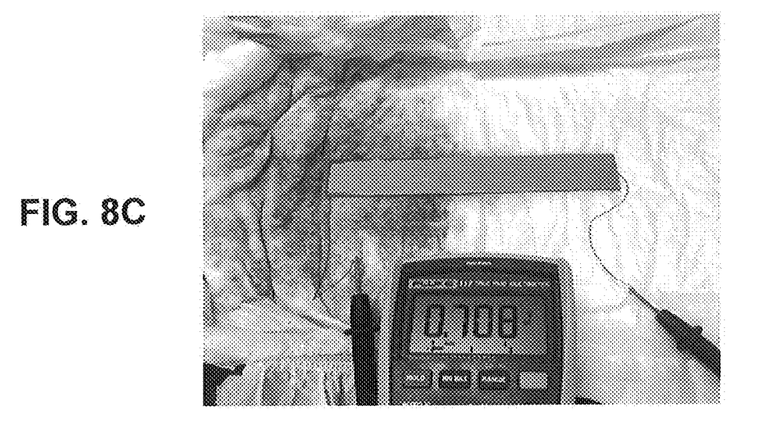

FIGS. 8a, 8b and 8c show morphology and voltage readings of the 4-electrochemical cell liquid sensor 802 disposed on a diaper 804, in various states of operation, in accordance with embodiments of the invention. Prior to addition of the electrolyte solution onto the diaper 804, the sensor strip was dry, and the voltage reading on multimeter 806 was approximately 2.16V. With the introduction of the electrolyte solution onto the diaper 804, the sensor 802 gradually became wet and its output voltage is decreased. For example, when the diaper 802 was partially wet as shown in FIG. 8b, the multimeter 806 that is connected to both ends of the liquid sensor 802 registers a reading of about 1.69V. As more solution was added, the diaper 804 became wetter, as indicated by shading shown on the diaper 804. Absorption of the electrolyte liquid by the sensor 802 is also significant, as shown by the damping of the sensor 802 at the edges. The sensor output voltage dropped to −0.7V. When additional liquid is poured such that the entire sensor 802 is immersed in liquid, the final voltage of the sensor output would be −0.5V (not shown).

Figure 9:
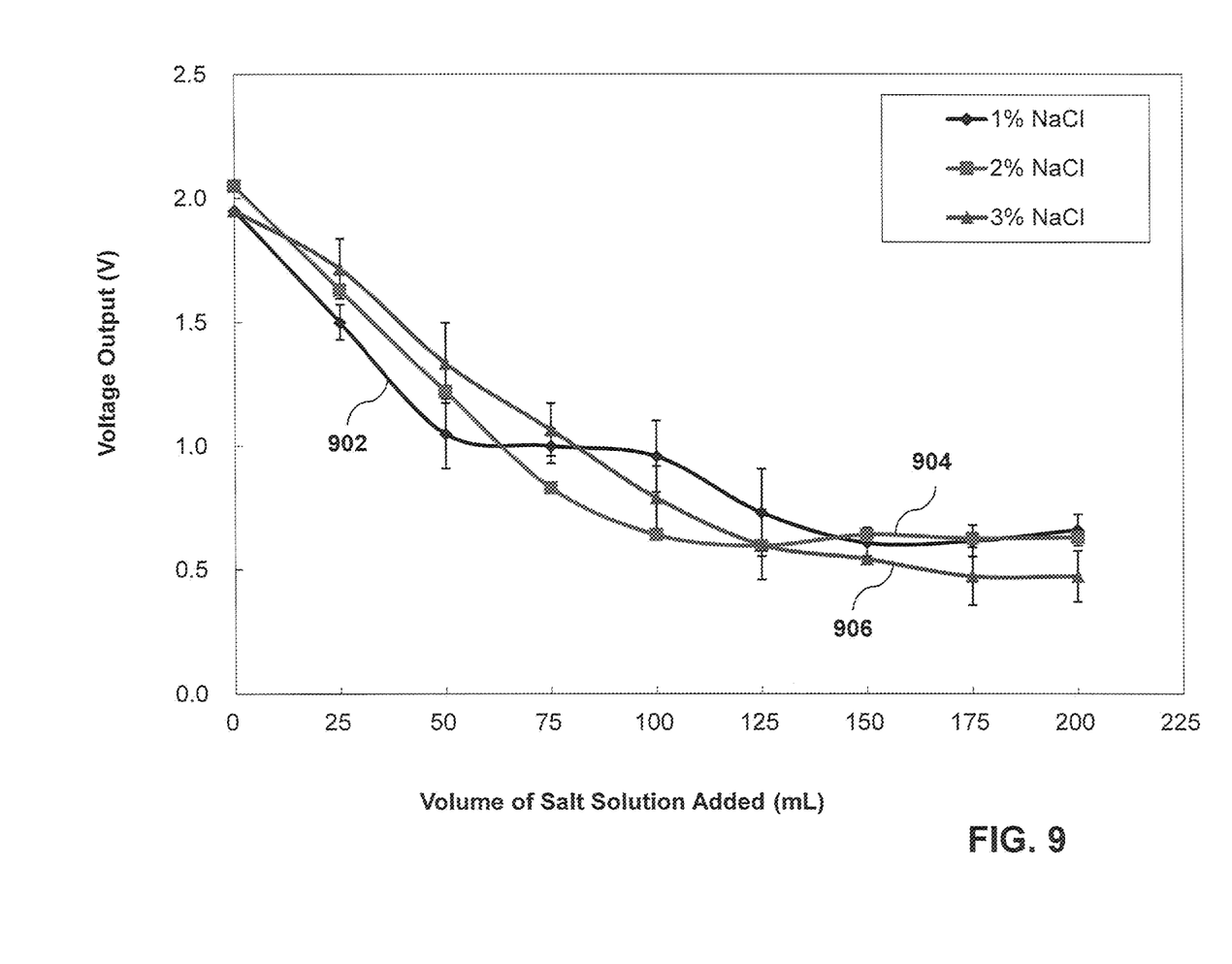
FIG. 9 shows a graphical representation of the relationship between volume of salt solution added and output voltage for example levels of salt concentration, in accordance with embodiments of the invention.

Additional quantitative results for the 4-electrochemical cell sensor strip 802 are shown in FIG. 9. FIG. 9 shows a graphical representation of the relationship between volume of salt solution added and output voltage for example levels of salt concentration, in accordance with embodiments of the invention. The salt concentration used is 1%, 2% and 3%, denoted by curves 902, 904, 906 respectively. The output voltage of the 4-electrochemical cell sensor strip 802 starts at −2V for all the 4 cells. The output voltage decreased gradually with the addition of salt solution to the diaper, until a stable value of −0.5V was reached (with all electrochemical 4 cells merged with solution as 1 cell) when a total of 150-200 mL of salt solution was introduced. As seen from FIG. 9, the voltage-volume change did not follow a linear relationship precisely, but can provide a qualitative indication of the amount of salt solution added. On the other hand, the concentration of the salt solution does not appear to have significant effects on the output voltage. This is desirable for the application of liquid sensor in diaper as human urine concentration may vary substantially depending on the hydration level of individuals.

Figure 10:
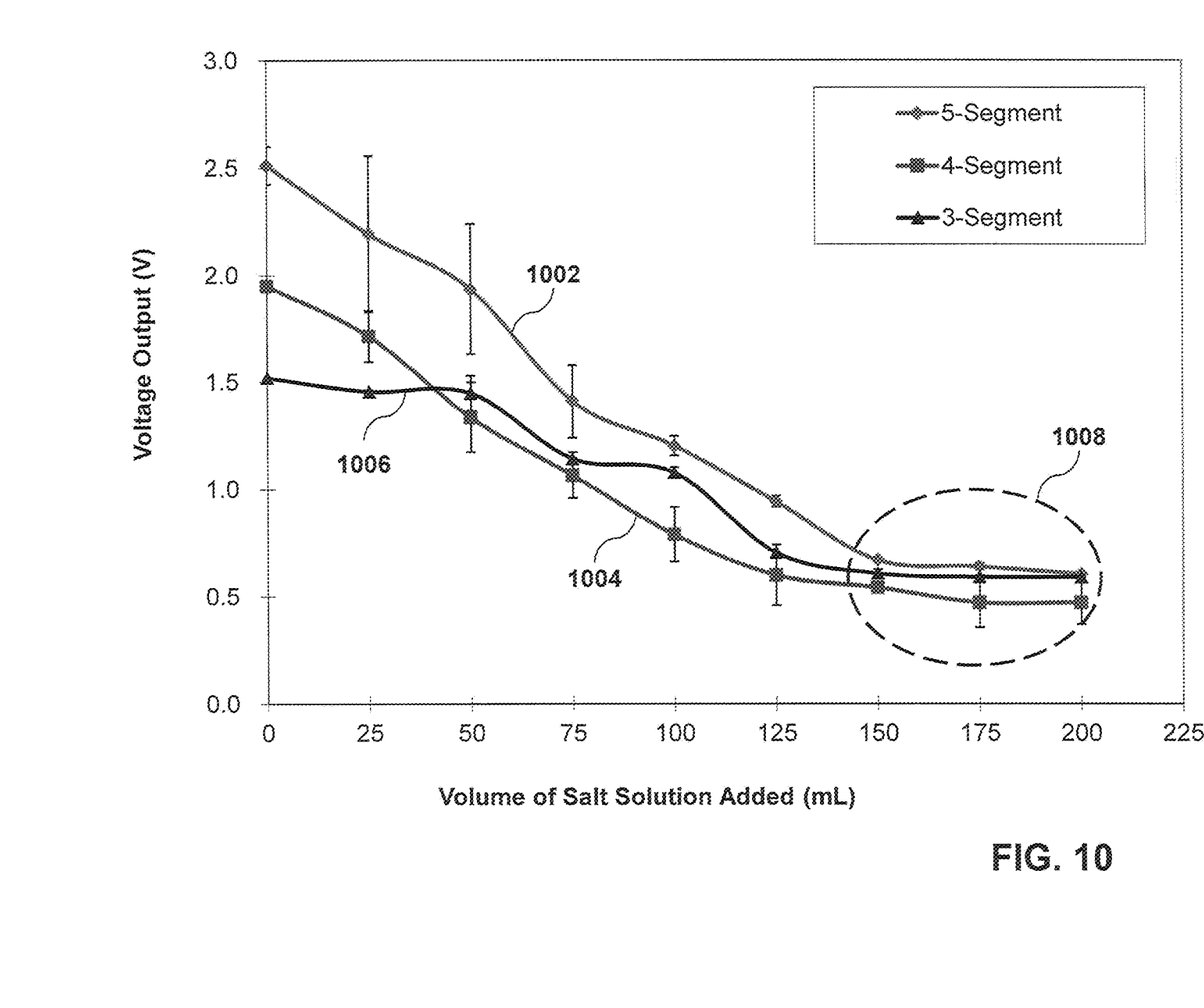
FIG. 10 shows a graphical representation of the relationship between volume of salt solution added and output voltage for example numbers of electrochemical cells, in accordance with embodiments of the invention.

FIG. 10 shows a graphical representation of the relationship between volume of salt solution added and output voltage for example numbers of electrochemical cells, in accordance with embodiments of the invention. The number of electrochemical cells (segments) used for the liquid sensors are 5, 4 and 3, denoted by 1002, 1004, 1006 respectively. The total length of the sensor strips are kept identical to ensure that the sensor strips are sufficient long enough to cover the same spatial distribution over a urine collection area of the diaper, whereby urine might be passed or accumulated. The initial output voltage is −2.5V, 2.0V and 1.5V for the 5-, 4- and 3-segment sensors respectively. It is noted that since the liquid sensors were of the same length, almost a similar amount of salt solution (~150 mL) was required to reach the 'fully wet' status, as indicated by the dashed circle 1008. The liquid sensors have approximately similar output voltage when the sensors are fully wetted (i.e. the individual electrochemical cells are connected by the liquid to form a single cell). As shown in FIG. 10, the change in the output voltage between the dry state and fully-wetted state is more significant for liquid sensors with more segments (i.e. electrochemical cells). In other words, liquid sensors with more electrochemical cells have a higher signal-to-noise ratio.

Figure 11:
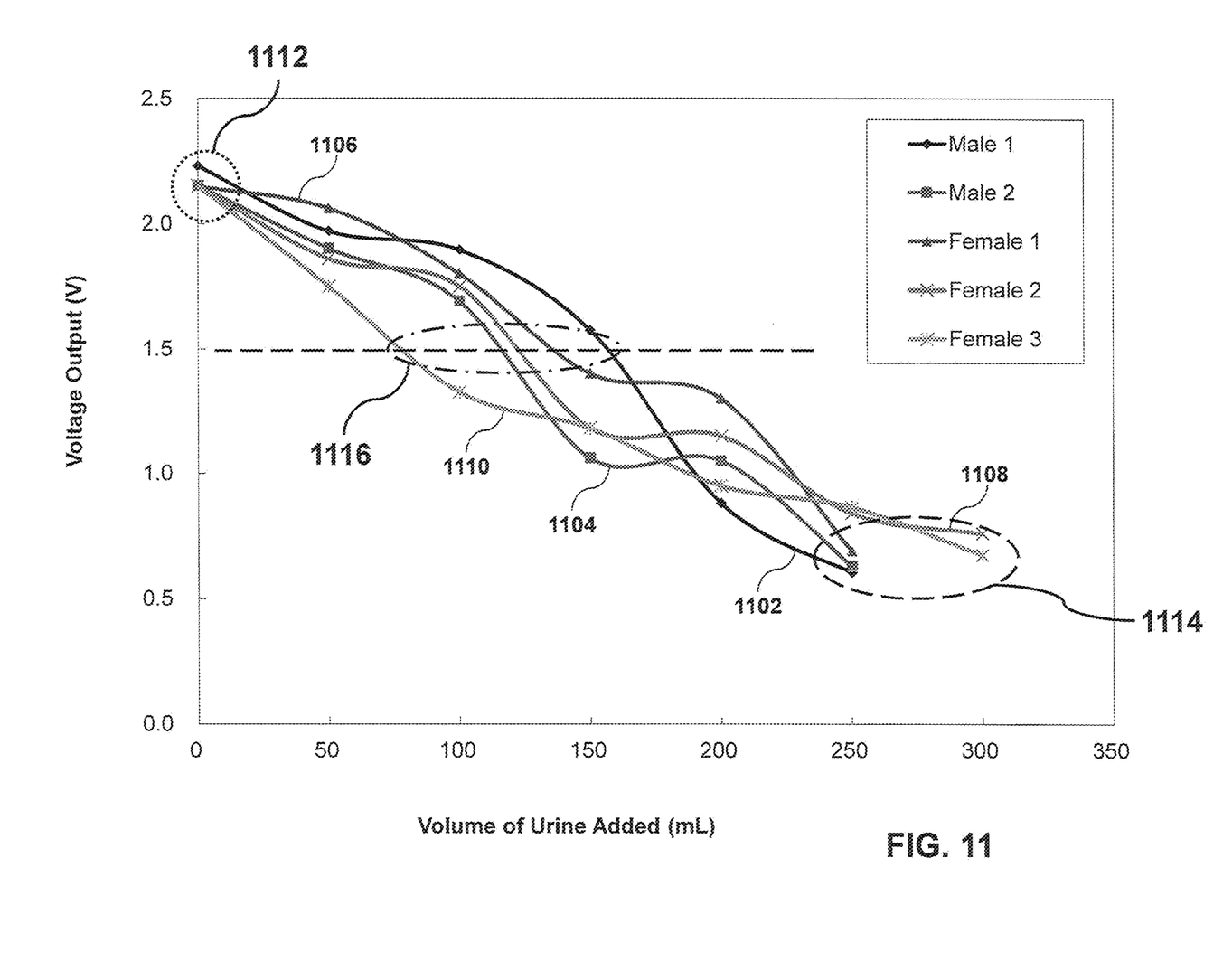
FIG. 11 shows a graphical representation of the relationship between volume of urine added and output voltage for example urine samples, in accordance with embodiments of the invention.

The prototype sensor strip was further characterized with human urine samples (see FIG. 11). FIG. 11 shows a graphical representation of the relationship between volume of urine added and output voltage for example urine samples, in accordance with embodiments of the invention. Two male urine samples, denoted by 1102, 1104 and three female urine samples, denoted by 1106, 1108, 1110 were used. Although there were some variations in the output voltage readings for different samples, the output voltage are deemed significant enough for qualitative assessment of the urine amount. For example, the output voltage ranged from between 2.1V to 2.3V for a dry diaper (as shown by dotted circle 1112), and between 0.6 V to 0.8 V (as shown by dashed circle 1114) for fully wetted diaper. A reading of 1.5V is associated with about 70-160 mL of urine passed to diaper (as shown by the dash-dot circle 1116).

Thus it can be seen that the liquid sensor in accordance with the present embodiments have the advantages of compactness, ease of production, low cost, high signal-to-noise ratio characteristics. While exemplary embodiments have been presented in the foregoing detailed description of the invention, it should be appreciated that a vast number of variations exist.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

The invention claimed is:

1. A liquid sensor for a diaper, the liquid sensor comprising:
   a plurality of electrochemical cells in series connection, each of the plurality of electrochemical cells comprising:
      an anode;
      a cathode; and
      a liquid-porous layer comprising an electrolyte solution, the liquid-porous layer electrically connecting the anode to the cathode such that each cell has a respective predetermined potential difference across the cell;
   wherein two or more of the plurality of electrochemical cells are operable to be electrically connected by a liquid to form a single electrochemical cell having a potential difference lower than the sum of the predetermined potential differences of the two or more electrochemical cells; and
   wherein the plurality of electrochemical cells are arranged laterally adjacent to each other to form a single layer film, and wherein the film is disposed on an insulated substrate.

2. The liquid sensor of claim 1, further comprising a removable seal encapsulating each of the plurality of electrochemical cells, wherein the seal is gas impermeable.

3. The liquid sensor of claim 1, wherein the hollow cylinder comprises a plurality of holes formed thereon.

4. The liquid sensor of claim 3, further comprising a voltage sensor connected to the first and second conductors, the voltage sensor configured to measure a potential difference of the plurality of electrochemical cells.

5. The liquid sensor of claim 1, wherein the anode comprises aluminum or zinc, and wherein the cathode comprises copper or graphite.

6. The liquid sensor of claim 1, wherein the liquid porous layer comprises one or more of a group consisting of: paper, cloth, polymeric absorbent, and silica gel.

7. The liquid sensor of claim 1, wherein the plurality of electrochemical cells are spatially distributed over a urine collection area of the diaper.

8. A method of detecting wetness of a diaper, the method comprising:
   disposing the liquid sensor of claim 1 such that the plurality of electrochemical cells are spatially distributed over a urine collection area of the diaper; and
   detecting a reduction in an output voltage of the plurality of electrochemical cells using a voltage sensor, wherein a magnitude of the reduction corresponds to a volume of the liquid dispensed onto the diaper.

9. A method of manufacturing a liquid sensor, the method comprising:
   providing a plurality of electrochemical cells, each of the plurality of electrochemical cells comprising:
      an anode;
      a cathode; and
      a liquid-porous layer comprising an electrolyte solution, the liquid-porous layer electrically connecting the anode and the cathode such that each cell has a respective predetermined potential difference across the cell; and
   connecting the plurality of electrochemical cells in series connection;
   wherein two or more of the plurality of electrochemical cells are electrically connectable by a liquid to form a single electrochemical cell having a potential difference lower than the sum of the predetermined potential differences of the two or more electrochemical cells; and
   wherein providing the plurality of electrochemical cells comprises:
      providing an insulated substrate; and
      disposing the plurality of electrochemical cells on the insulated substrate such that the plurality of electrochemical cells are arranged laterally adjacent to each other to form a single layer film.

10. The method of claim 9, further comprising encapsulating each of the plurality of electrochemical cells with a removable seal, wherein the seal is gas impermeable.

11. The method of claim 9, further comprising electrically connecting a first conductor to one end of the plurality of electrochemical cells and a second conductor to another end of the plurality of electrochemical cells.

12. The method of claim 9, wherein the anode comprises aluminum or zinc, and wherein the cathode comprises copper or graphite.

13. The method of claim 9, wherein the liquid porous layer comprises one or more of a group consisting of: paper, cloth, polymeric absorbent and silica gel.

* * * * *

UNITED STATES PATENT AND TRADEMARK OFFICE
CERTIFICATE OF CORRECTION

PATENT NO. : 11,166,857 B2
APPLICATION NO. : 16/484888
DATED : November 9, 2021
INVENTOR(S) : Jackie Y. Ying et al.

It is certified that error appears in the above-identified patent and that said Letters Patent is hereby corrected as shown below:

In the Claims

At Column 12, Lines 20-21, in Claim 3, "3. The liquid sensor of claim 1, further comprising a removable seal encapsulating each of the plurality of electrochemical cells, wherein the seal is gas impermeable." should be -- 3. The liquid sensor of claim 1, further comprising a first conductor electrically connected to one end of the plurality of electrochemical cells and a second conductor electrically connected to another end of the plurality of electrochemical cells. --.

Signed and Sealed this
Twenty-sixth Day of April, 2022

Katherine Kelly Vidal
*Director of the United States Patent and Trademark Office*